US007542913B1

(12) United States Patent
Meek et al.

(10) Patent No.: US 7,542,913 B1
(45) Date of Patent: Jun. 2, 2009

(54) SYSTEM AND METHOD OF PREDICTING HIGH UTILIZERS OF HEALTHCARE SERVICES

(75) Inventors: Julie A. Meek, Greenwood, IN (US);
Brenda L. Lyon, Indianapolis, IN (US);
Wendy D. Lynch, Lakewood, CO (US)

(73) Assignee: CareGuide, Inc., Coral Springs, FL (US)

( * ) Notice: Subject to any disclaimer, the term of this patent is extended or adjusted under 35 U.S.C. 154(b) by 0 days.

(21) Appl. No.: 09/520,419

(22) Filed: Mar. 8, 2000

(51) Int. Cl.
*G06Q 40/00* (2006.01)

(52) U.S. Cl. .................. 705/4; 705/2; 705/3; 600/300; 600/301; 128/920; 128/921; 128/922; 128/923; 128/924

(58) Field of Classification Search ............... 705/2–4, 705/10; 600/300–301; 128/920, 921, 922, 128/923, 924
See application file for complete search history.

(56) References Cited

U.S. PATENT DOCUMENTS

| | | | | |
|---|---|---|---|---|
| 4,464,122 A | * | 8/1984 | Fuller et al. ................ | 434/262 |
| 4,975,840 A | * | 12/1990 | DeTore et al. ............... | 705/4 |
| 5,276,612 A | | 1/1994 | Selker ........................ | 600/523 |
| 5,435,324 A | * | 7/1995 | Brill ........................... | 128/897 |
| 5,471,382 A | | 11/1995 | Tallman et al. .............. | 600/300 |
| 5,486,999 A | * | 1/1996 | Mebane ....................... | 705/2 |
| 5,572,421 A | | 11/1996 | Altman et al. ............... | 705/3 |
| 5,692,501 A | | 12/1997 | Minturn ...................... | 600/301 |
| 5,764,923 A | | 6/1998 | Tallman et al. .............. | 705/3 |
| 5,799,101 A | | 8/1998 | Lee et al. .................... | 382/133 |
| 5,940,802 A | | 8/1999 | Hildebrand et al. .......... | 705/3 |
| 5,967,559 A | | 10/1999 | Abramowitz ................ | 283/67 |
| 5,976,082 A | * | 11/1999 | Wong et al. ................. | 600/300 |
| 6,059,724 A | * | 5/2000 | Campell et al. ............. | 600/300 |
| 6,061,657 A | * | 5/2000 | Whiting-O'Keefe ......... | 705/2 |
| 6,110,109 A | * | 8/2000 | Hu et al. ..................... | 600/300 |
| 6,234,964 B1 | * | 5/2001 | Iliff ............................ | 600/300 |
| 6,269,339 B1 | * | 7/2001 | Silver ......................... | 705/2 |
| 6,385,589 B1 | * | 5/2002 | Trusheim et al. ............ | 705/2 |
| 6,484,144 B2 | * | 11/2002 | Martin et al. ................ | 705/2 |
| 2001/0020229 A1 | * | 9/2001 | Lash ........................... | 705/3 |

OTHER PUBLICATIONS

Predicting the Demand For Healthcare, Lynch, Wendy D C; Edington, DW, Johnson, Alan; The Healthcare Forum Journal; Jan./Feb. 1996; 39,1.*
IRIS Question Set (seven page booklet).
IRIS Formula (11 pages).
Mindstretcher: Logistic regression explained (Mar. 1997; 37-5) 2 pages.
Office of Statistical Consulting, Aug. 12, 1996, 2 pages.
Chi Square Tutorial, 8 pages.

* cited by examiner

*Primary Examiner*—C Luke Gilligan
*Assistant Examiner*—R. David Rines
(74) *Attorney, Agent, or Firm*—Bose McKinney & Evans

(57) ABSTRACT

A healthcare management system and method identify individuals at risk of high near-term healthcare use. On step of the method includes collecting information from an individual for a predetermined set of predictive factors. Another step of the method includes assigning, based upon the information from the individual, a separate value to each predictive factor of the predetermined set of predictive factors. The method further includes the step of generating, based upon a predetermined predictive model and the separate values assigned to the predetermined set of predictive factors, a risk level of the individual utilizing healthcare services at a predetermined level within a prospective time span.

19 Claims, 3 Drawing Sheets

SYSTEM AND METHOD OF PREDICTING HIGH UTILIZERS OF HEALTHCARE SERVICES

FIELD OF THE INVENTION

The present invention relates generally to healthcare management systems, and more particularly to a healthcare management system and method for identifying individuals at risk for high near-term healthcare use.

BACKGROUND OF THE INVENTION

In commercial adult managed care populations, typically 10-20% of the population will incur 80-90% of the risk exposure for the risk-bearing payer. A major challenge in today's managed care environment is prospectively predicting which members are at risk for high utilization to enable appropriate targeting of proactive case management and intervention programs. These members could enjoy better health and incur fewer health-related expenses if they could be identified early and managed proactively.

Historically over the last 30 years, health assessment tools for adult populations (18-65 years of age) have been built upon clinical risk/chronic disease models to guide clinical decision making, to serve as outcome measures, or to automate aspects of care such as automated problem lists, laboratory results, and healthcare reminders. The emphasis has been on practical clinical issues, resulting in limited predictive power in terms of targeting those at risk for higher levels of healthcare-seeking behavior.

Increasingly, the ability of risk-bearing payers to approach population health management in a cost and quality-effective manner, will be dependent upon sound predictive models which guide care toward members who have a higher probability of becoming a high care user in the near-term. Adding momentum to the efforts, technological advances such as ASP and dynamic HTML Web tools, widespread connectivity to the Internet, and digital, variable-data print technologies have only recently become available to make population-based care management a real option versus a rhetorical question.

Theoretically and empirically, evidence suggests that near-term healthcare utilization may not be as strongly tied to traditional disease and clinical risk models as once thought. Indeed, 40-60% of office visits are often tied to non-disease based concerns. Also, from a practical perspective, risk/disease models often miss key prescriptive data which may guide the health counseling process (i.e., areas of readiness to change, stress levels, levels of perceived self-management, etc.) and key outcome measures (i.e., improvements in functional ability, levels of stress emotions, disease and medication compliance, etc.). In a practical sense, claims-based stratification methods are limited by the inherent inadequacies of the claims data itself, including the lack of claims history from new enrollees and the several month time lags often required to access and process the predictive information.

Therefore, a need exists for a healthcare management system and method that identify, based upon easily ascertained self-reported information, those members of a managed healthcare group who are at risk for high near-term healthcare use

SUMMARY OF THE INVENTION

The present invention addresses the above-identified need, as well as others, with a method of managing healthcare services. On step of the method includes collecting information from an individual for a predetermined set of predictive factors. Another step of the method includes assigning, based upon the information from the individual, a separate value to each predictive factor of the predetermined set of predictive factors. The method further includes the step of generating, based upon a predetermined predictive model and the separate values assigned to the predetermined set of predictive factors, a risk level of the individual utilizing healthcare services at a predetermined level within a prospective time span.

Pursuant to another embodiment of the present invention, there is provided a healthcare management system including a processor, and a memory operably coupled to the processor. The memory includes instructions that, when executed by the processor, cause the processor to assign, based upon information from an individual, a separate value to each predictive factor of a set of predictive factors. The instructions of the memory, when executed by the processor, further cause the processor to generate, based upon a predetermined predictive model and the separate values assigned to the predetermined set of predictive factors, a risk level of the individual utilizing healthcare services at a predetermined level within a prospective time span.

Pursuant to a further embodiment of the present invention, there is provided a computer readable medium for a healthcare management system. The computer readable medium including instructions that, when executed by the healthcare management system, cause the healthcare management system to assign, based upon information from an individual, a separate value to each predictive factor of a set of predictive factors. The instructions, when executed by the healthcare management system, further cause the healthcare management system to generate, based upon a predetermined predictive model and the separate values assigned to the predetermined set of predictive factors, a risk level of the individual utilizing healthcare services at a predetermined level within a prospective time span.

It is an object of the present invention to provide an improved healthcare management system and method.

It is also an object of the present invention to provide a new and useful healthcare management system and method.

It is another object of the present invention to provide a healthcare management system and method for identifying high risk individual users of healthcare services.

It is yet another object of the present invention to provide a computer readable medium for configuring a healthcare management system to identify individuals at risk of high near-term healthcare use.

It is yet another object of the present invention to provide a healthcare management system and method for identifying members of a managed care group who are at risk to utilize healthcare services at a predetermined usage rate within prospective time span.

The above and other objects, features, and advantages of the present invention will become apparent from the following description and the attached drawings.

DESCRIPTION OF EXEMPLARY EMBODIMENTS

Figure 1:
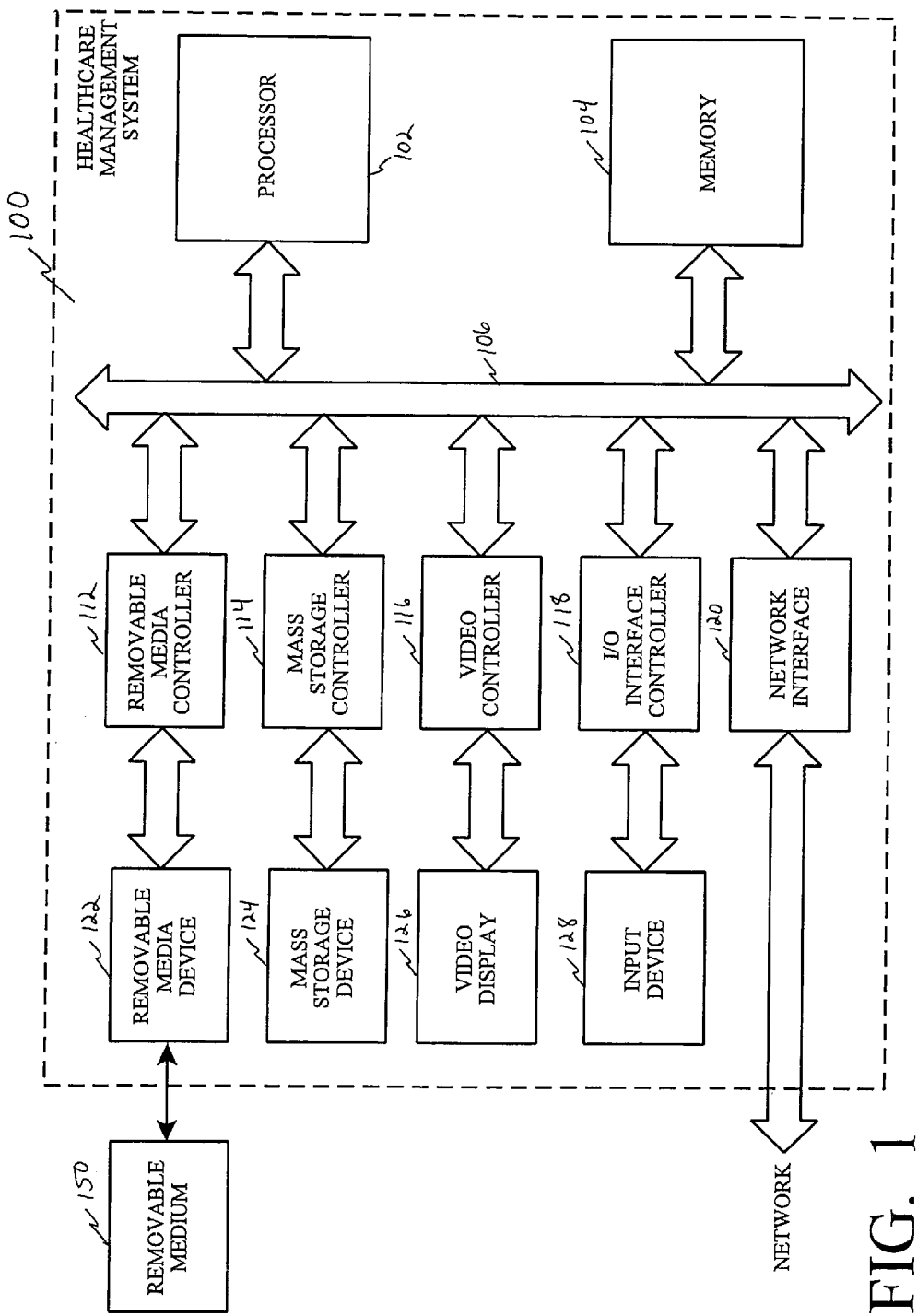
FIG. 1 is a simplified block diagram of an exemplary healthcare management system which incorporates various features of the present invention.

While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Referring now to FIG. 1, a simplified block diagram of an exemplary healthcare management system ("HMS") 100 is shown which incorporates various features of the present invention. As will be explained in more detail, the exemplary HMS 100 is generally operable to identify members (i.e. individuals), based upon perceived health information, who are at risk of high near-term healthcare use. Besides identifying members of the managed care group who are at risk for high near-term healthcare use, the HMS 100 enables proactive case management of the identified members. For example, the HMS 100 enables healthcare managers identify individuals who are at risk of incurring significant healthcare expenses in the near-term so that intervention programs may be targeted to these identified individuals in order to help these individuals to enjoy better health and to incur fewer health-related expenses.

To this end, the exemplary HMS 100 includes a processor 102, memory 104, a system bus 106, controllers 112, 114, 116, 118, network interface 120, and devices 122, 124, 126, 128. The hardware architecture of the exemplary HMS 100 is generally illustrative of general purpose computing systems such as personal computers, workstations, and servers currently manufactured by Gateway, Dell, Macintosh, Sun Microsystems, and IBM. While the hardware architecture of the exemplary HMS 100 is generally illustrative of general purpose computing systems, the HMS 100 may also be implemented as a special purpose computing device that is generally operable to perform a limited set of tasks associated with healthcare management.

Returning to the description of the exemplary HMS 100, the processor 102 includes one or more processing units such as the central processing units of Intel, AMD, IBM, National Semiconductor, and Transmeta. The processor 102 is generally operable to execute software and/or firmware routines stored in the memory 104. As a result of executing the software and/or firmware routines of the memory 104, the processor 102 controls the general operation of the HMS 100 and the devices 122, 124, 126, 128 via the respective controllers 112, 114, 116, 118. Moreover, the processor 102 as a result of executing software and/or firmware routines of the memory 104 is generally operable to implement a predictive model that identifies, based upon perceived health, members of a managed care group who are at risk of high near-term healthcare use.

The memory 104 of the exemplary HMS 100 is operable to store data and code used by the processor 102. To this end, the memory 104, in an exemplary embodiment, includes standard random access memory for storing the data and software code needed by the processor 102. However, the memory 104 may alternatively include other volatile memory types such as DRAM, SDRAM, and SRAM for storing data and software code and/or non-volatile memory such as ROMs, PROMs, EEPROMs, and flash memory for storing data and firmware code.

The system bus 106 is generally operable to interconnect the processor 102, the memory 104, and the controllers 112, 114, 116, 118. To this end, the system bus 106 in the exemplary embodiment includes an address bus and data bus which enable the various components of the exemplary HMS 100 to communicate with one another.

The removable media drive 122 is generally operable to read information from and write information to the removable storage medium 150, and the removable storage media controller 112 is generally operable to provide the processor 102 with an interface to the removable media drive 122. The removable media drive 122 may include various computer readable and/or writeable storage media devices such as floppy disk drives, DVD drives, tape drives, DAT drives, and ZIP drives in order to access corresponding types of removable storage media. The removable media drive 122 may also include non-volatile memory interfaces for accessing non-volatile memory devices such as PROMS, EEPROMS, and Flash Memory.

The mass storage device 124 is generally operable to store data and/or software code of the exemplary HMS 100, and the mass storage controller 114 is generally operable to provide the processor 102 with an interface to the data and/or software code stored by the mass storage device 118. To this end, the mass storage device 118 may include various computer readable and/or writeable media devices such as hard disk drives, floppy disk drives, CD-ROM drives, DVD-RAM drives, RAID devices, and/or Disk-On Chip devices to name a few. The HMS 100 may alternatively be implemented without a mass storage device 122 and mass storage controller 112. For example, the exemplary HMS 100 may be implemented with data and firmware code stored in a non-volatile manner in the memory 104.

The video display device 126 is operable to provide a visual display to a user of the exemplary HMS 100, and the video controller 116 is operable to provide the processor 102 with an interface to the video display device 126. To this end, the video display device 126 may include CRT displays, LCD displays, and/or standard television displays. The HMS 100 may alternatively be implemented without a video display device 126, and video controller 116. For example, the HMS 100 may be implemented to output results to an attached printer (not shown), the removable storage media 150, and/or another computing device attached to the HMS 100 via the network interface 120, a USB port (not shown), parallel port (not shown), or FireWire interface (not shown).

The input device 128 is operable to provide a user of the exemplary HMS 100 with an interface to control the operation of the exemplary HMS 100 and/or to provide the exemplary HMS 100 with information. Moreover, the I/O interface controller 118 is operable to provide the processor 102 with an interface to the input device 128. To this end, the input device may include a mouse, keyboard, touch pad, push buttons, touch screen, and/or digital scanner.

The network interface 120 is generally operable to couple the exemplary HMS 100 to a network such as the Internet, an intranet, and/or an extranet. The network interface 120 generally enables the exemplary HMS 100 to send and receive information to and from other computing devices coupled to the network. To this end, the network interface 120 may be implemented with a network interface card such as an Ethernet card or Token Ring card. The network interface 120 may also be implemented with an analog modem for use over POTS telephone lines such as a 28.8K or 56K modem. The network interface 120 may also be implemented with a digital modem such as a cable modem for use over a cable distribution network, an ISDN modem for use over an ISDN telephone line, or a DSL modem for use over a POTS telephone lines that support DSL.

Figure 2:
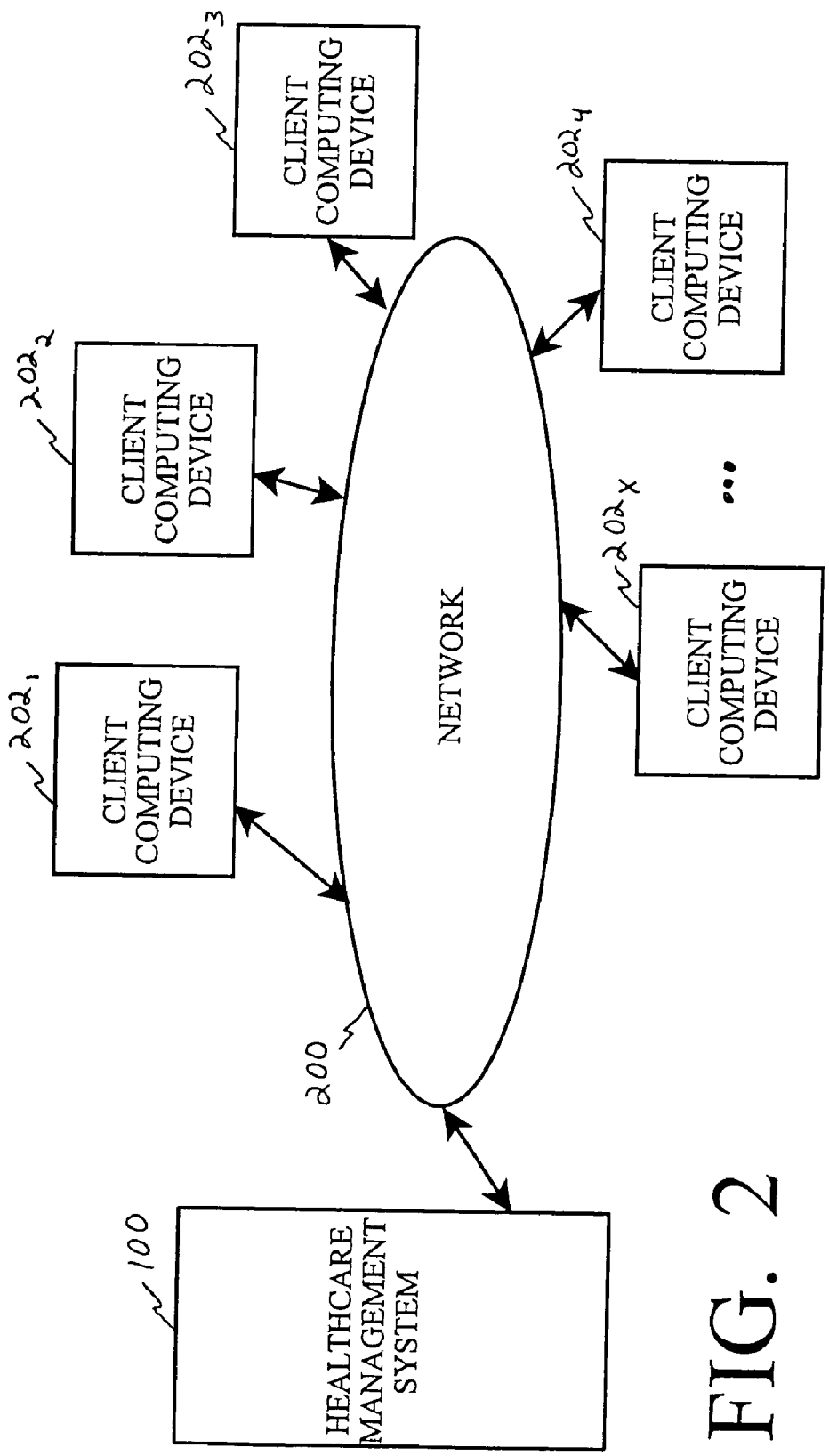
FIG. 2 illustrates an exemplary operating environment in which the healthcare management system of FIG. 1 may be utilized.

An exemplary operating environment is illustrated in FIG. 2. As illustrated, the HMS 100 is operably coupled to client computing devices $202_1, 202_2 \ldots 202_X$ via a network 200. The network 200 may include multiple public or private LANs and/or WANs that are operably coupled to one another via routers, switches, hubs, gateways, proxies, and/or firewalls. In an exemplary embodiment, the network interface 120 of the HMS 100 is operably coupled to a LAN that provides a gateway to the Internet. As a result, the exemplary HMS 100 is accessible to client computing devices $202_1, 202_2 \ldots 202_X$ that are either coupled to the LAN or the Internet, thus providing the services of the HMS 100 to people located locally and throughout the world.

In an exemplary embodiment, the HMS 100 communicates with client computing devices $202_1, 202_2 \ldots 202_X$ in accordance with the Hyper Text Transport Protocol (HTTP) and other Internet Protocols (IP). Accordingly, the services of the HMS 100 are generally available to any client computing device that supports the appropriate IP protocols. Most personal computers such as those manufactured by Dell and MacIntosh include web browsing software that provide an interface to services delivered via the IP protocols. However, besides personal computers, many other devices are being developed that include web browsing capabilities. For example, set-top boxes such as Microsoft's WebTV and certain digital mobile phones include web browsing capabilities and could be used to access the services of the HMS 100.

As stated above, the HMS 100 identifies individuals who are at risk of high near-term healthcare use based upon perceived health information and other information. Perceived health is defined as a person's composite evaluation of how he or she is feeling and doing. People experience health as either some level of wellness or illness. If a person is experiencing unpleasant or uncomfortable physical sensations and/or emotions in addition to not functioning up to their perceived capability level, the person perceives some level of illness. Some degree of wellness, on the other hand, is perceived when the person experiences pleasant/comfortable physical sensations and emotions combined with an acceptable level of self-evaluated functioning.

The difference between the perceived health and disease/risk models is that a person can experience wellness in the presence or absence of disease. For example, a person who has diabetes can experience wellness in that from the persons's perspective the person is feeling and doing well. Conversely, a person can experience illness in the absence of discernable disease in that from the person's perspective the person is not feeling nor doing well. From a practical viewpoint, people seek care when their sense of feeling and doing is below their perceived threshold of tolerance.

Evidence also shows a correlation between (i) an individual's beliefs and preferences regarding the healthcare system and (ii) particular types of healthcare-seeking behavior. In particular, individuals who place high levels of faith in the healthcare system or desire the input of health professionals to make health decisions tend to use the healthcare system more often.

Figure 3:
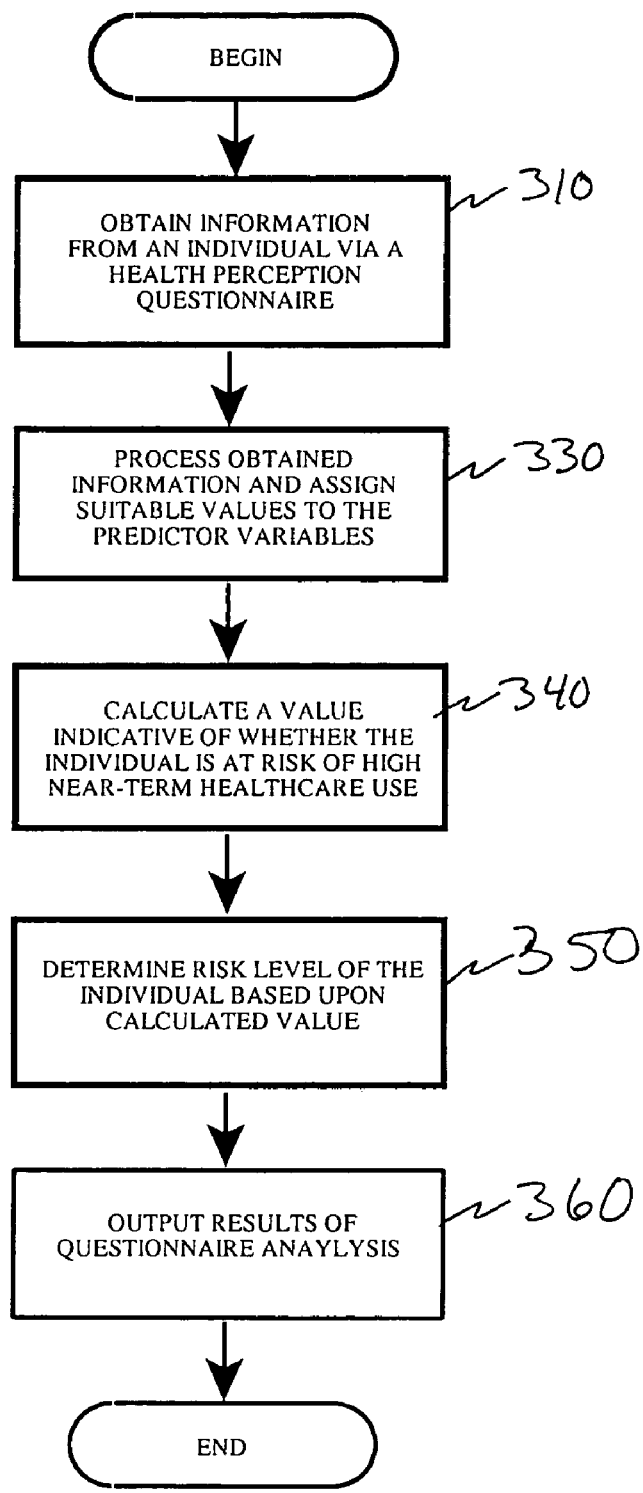
FIG. 3 is a flowchart depicting the general operation of the healthcare management system of FIG. 1.

As a result of the above observed correlations, the exemplary HMS 100 attempts to identify individuals at risk of high near-term healthcare use based upon information about an individual's perceived health, beliefs and preferences regarding the healthcare system, past levels of healthcare use, and demographics. To this end, the HMS 100 in step 310 of FIG. 3 obtains such information from an individual via a health perception questionnaire. An exemplary questionnaire is provided in Appendix A and includes questions that elicit information for a predetermined set of predictive factors which include past healthcare use factors, demographic factors, perceived health factors, disease factors, healthcare compliance factors, healthcare belief factors, and healthcare preference factors.

The exemplary HMS 100 is operable to display the health perception questionnaire on the video display 126 and receives responses to the questions of the questionnaire via the input device 128. Moreover, the exemplary HMS 100 is further operable to transmit the questionnaire to client computing devices $202_1, 202_2 \ldots 202_X$ via the network 200, and receives responses to the questions of the questionnaire from client computing devices $202_1, 202_2 \ldots 202_X$ via the network 200. The HMS 100 may also include various other mechanisms for receiving responses to the health perception questionnaire. For example, the HMS 100 may include a digital scanner that is operable to read from a printed questionnaire an individual's responses to the questions of the questionnaire. The HMS 100 may also obtain responses to the questionnaire from archived information stored on a removable medium 150, the mass storage device 124, or a database accessible via the network 200. Further yet, them HMS 100 may obtain responses to the questionnaire via telephone (e.g. an interactive voice response telephone system).

After obtaining information from an individual, the exemplary HMS 100 analyzes the information based upon a predictive model developed from similar information collected from other individuals and their prospective use of healthcare services. As will be explained in more detail below, the exemplary HMS 100 analyzes the information based upon a logistic regression predictive model represented by the following equations:

$$z = \beta_1 X_1 + \beta_2 X_2 + \beta_3 X_3 + \beta_4 X_4 \ldots \beta_{38} X_{38} + \beta_{39} X_1 X_2 + C,$$

$$P_{high\_use} = e^z/(1+e^z)$$

where $\beta_1, \beta_2, \beta_3, \beta_4 \ldots \beta_{39}$ represent the regression coefficient shown in Table 2 of Appendix B; $X_1, X_2, X_3, X_4 \ldots X_{38}$ represent the predictor variables shown in the questionnaire of Appendix A and Table 2 of Appendix B; and C represents the regression constant shown in Table 2 of Appendix B. Those skilled in the art should appreciate that predictor variables $X_1$ and $X_2$ are interaction variables. Moreover, other analysis tools such as neural networks, genetic algorithms, and fuzzy logic could also be used to develop the predictive model.

In order to utilize the above logistic regression predictive model, the exemplary HMS 100 in step 330 processes an individual's responses to the health perception questionnaire in order to obtain suitable values for the predictor variables $X_1, X_2, X_3, X_4 \ldots X_{38}$. More specifically, the predictor variables $X_1, X_2, X_3, X_4 \ldots X_{38}$ of the logistic regression are converted to dichotomous variables (i.e. variables that can have one of only two values such as 0 or 1). Accordingly, the exemplary HMS 100 assigns an appropriate dichotomous value to each of the predictor variables $X_1, X_2, X_3, X_4 \ldots X_{38}$ based upon the responses to the health perception questionnaire. In the exemplary embodiment, the HMS 100 generally assigns a first dichotomous value of "0" to each variable $X_1, X_2, X_3, X_4 \ldots X_{38}$ that the responses suggest are not indicative of the individual being at risk of high near-term healthcare use, and assigns a second dichotomous value of "1" to each variable $X_1, X_2, X_3, X_4 \ldots X_{38}$ that the responses suggest are indicative of the individual being at risk of high near-term healthcare use. Table 2 of Appendix B illustrates the possible responses to the questionnaire for each predictive variable and corresponding dichotomous value assigned to the predictive variable $X_1, X_2, X_3, X_4 \ldots X_{38}$. Moreover, for each variable each variable $X_1, X_2, X_3, X_4 \ldots X_{38}$ corresponding to an answered or an inappropriately answered question, the exemplary HMS 100 assigns the variable a value of "0" in order to be conservative in identifying individuals as high near-term users of healthcare services.

After assigning a dichotomous value to each of the predictor variables $X_1, X_2, X_3, X_4 \ldots X_{38}$, the HMS 100 in step 340 calculates, based upon the above logistic regression equations, a value indicative of whether the individual is at risk of high near-term healthcare use. Essentially, the exemplary HMS 100 in step 340 obtains for the individual a probability value, ranging between 0 and 1, that is indicative of the probability that the individual is a high-risk for high near-term healthcare use.

The HMS 100 then in step 350 determines based upon the probability value obtained for the individual in step 340 whether the individual should be identified as a high-risk or a low-risk person. In particular, the exemplary HMS 100 makes such a determination by comparing the obtained probability value to a predetermined threshold value. The threshold value is preselected to strike a balance between sensitivity and specificity of the measurement. Sensitivity is defined as the percent of people who become high care users and are so identified prospectively by the predictive formula. Specificity is defined as the percent of people who do not become high care users and are so identified by the formula. From a practical viewpoint, the threshold value may also be selected dependent upon the sponsoring plan's objectives, intervention capacity, financial parameters, and expectations. The exemplary HMS 100 utilizes a threshold value of 0.47 and identifies any individual with a probability value greater than the threshold value as a high-risk of high near-term healthcare use. Furthermore, besides identifying an individual as a high-risk if their associated probability value $P_{high\_user}$ exceeds the threshold value, the exemplary HMS 100 also marks an individual as a high risk if the individual fails to answer or incorrectly answers more than a predetermined number of questions.

The HMS 100 in step 360 outputs the results of the analysis. In particular, the exemplary HMS 100 is operable to display output results on video display 126 or transmit the output results to a client computing device $202_1, 202_2 \ldots 202_X$ for display. In the exemplary embodiment, the HMS 100 is operable to generate several types of reports and restrict the generation of certain reports to authorized personnel. For example, a member of the managed care group (i.e. an individual responding to the health perception questionnaire) may cause the HMS 100 to generate reports which (i) provide a general health report, (ii) advise as to how the individual may improve their overall health, (iii) provide information about appropriate intervention programs, and (iv) provide follow-up coaching reports from care providers. On the other hand, personnel of a managed care group may cause the HMS 100 to later generate similar reports about the above identified member and additional reports that (i) summarize the wellness of the managed care group, (ii) list individuals identified as high risk, and (iii) identify intervention programs which address wellness needs of the managed care group.

Development and Validation of the Exemplary Predictive Model

The predictive model of the exemplary HMS 100 was developed from an initial member population of 20,000 members ages 18-65 with claims data showing more than 6 primary care visits within the last year. A health perception questionnaire containing 70 question/126 response was mailed to the 20,000 members. Subsequently, for the 5,285 members who responded, claims data were obtained from the health plan for the next six months yielding 4,271 members who responded to the health perception questionnaire and were also continuously enrolled during the entire study time period. Those members who completed an intervention program targeted to high utilizers (N=61) were removed from subsequent analyses, leaving 4,210 for the final sample. The sample included 3 female respondents for every male respondent. To assure that the predictive model was developed for a gender-representative population, cases were weighted (3:1) to approximate the normal gender distribution of 51.2% female to 48.8% male. Both the original and weighted sample descriptives are listed in Table 1 of Appendix B.

As indicated above, logistic regression was selected for developing the predictive model; however, other analysis tools such as neural networks, genetic algorithms, and fuzzy logic could also be used to develop the predictive model. Logistic regression is especially suited for highly skewed data such as the six-month claims encounter data. For this reason, members confirmed as outliers in terms of six-month total dollars or encounters were left in the data set, because the conversion to a dichotomous variable mitigates the outlier effect.

To prepare all questionnaire information for logistic analysis, each survey item of the questionnaire was converted to a dichotomous variable with a value of "0" indicating low-risk and a value of "1" indicating high-risk responses for each item. In cases where item responses could not be conceptually categorized as high-risk versus low-risk, analyses were run comparing responses with subsequent care use to determine the final coding. All missing survey item data (<10% on each variable) was coded as "0" to be conservative.

"Total encounters" over the subsequent six-month period was chosen as the dependent variable. An encounter was defined as a unique person with a unique provider on a unique date. Thus for example, if a person went to their physician, was subsequently sent to a lab and finally to pick up a prescription, the total encounters would equal three. With the impact of DRG's on hospital stays and the increasing movement of services to the outpatient and office settings, this definition of encounters was felt to more accurately represent total healthcare use with accompanying total dollars.

The decision to dichotomize the dependent variable, essentially deciding where to mark the cut-off for a high (1) versus low (0) care user, was a more difficult challenge. A practical rule was used that compares the percent of the population with the percent of premium dollar used. What seems to occur with regularity across adult commercial populations is that the top 2% of care users utilize 40% of the premium, the next 18% of high care users utilize the next 40% of the premium;

the next 65% of the members will use the remaining 20% of the premium and 15% of the population will have no care use within the given year. The total member population for the health plan at that time was 36,354 people.

The sample population was ranked from highest to lowest based upon total claims dollars, and each segment of the above identified segments were then weighted until the population reached 36,354. Subsequently, the resulting data set was checked to assure that the percentage of the population coincided with the percent of premium dollar used. Using this method, 3.6% of the extrapolated population used the first 40% of the premium and 22.3% used the next 40% of the premium. By observing the mean, median and range of encounters for this combined 25.9% group versus all others in the population, the dependent variable cut-off was determined to be 6 or greater encounters in a six month period as the high-risk group coded as "1".

After the dependent variable and all of the potential predictor variables were coded with dichotomous values, logistic regression was applied using all perceived health, risk, disease, compliance, belief/preference and demographic variables. A split-half technique was used where the predictive model is developed on a randomly selected first half of the data set (N=2,067) and then tested for its stability on the second half of the population (N=2,143). Using standard logistic regression on the first split-half of the weighted sample, 50 variables were found to have significance levels at 0.25 or less including 3 interaction variables in the initial analysis. Subsequent to this initial analysis, a forward stepwise regression was run using these 50 variables on the first split-half, with 39 variables entering the equation. The results of the forward stepwise logistic regression of the probability of becoming a high encounter member using the 39 final predictor variables on the first split-half are shown in Table 2 of Appendix B. The obtained logistic model correctly predicted 68.08% of the observed high care use group and 61.93% of the observed low care use group.

Next, the predictive model was converted to a formula, which could be used to test the first and second split-halves. First, the formula calculates each person's probability ($P_{high\_use}$) of becoming a high care user by inserting his or her responses to the 39-predictor variables into the logistic formula:

$$z = \beta_1 X_1 + \beta_2 X_2 + \beta_3 X_3 + \beta_4 X_4 \ldots \beta_{38} X_{38} + \beta_{39} X_1 X_2 + C,$$

$$P_{high\_use} = e^z/(1+e^z)$$

where $\beta_1, \beta_2, \beta_3, \beta_4 \ldots \beta_{39}$ represent the regression coefficient shown in Table 2 of Appendix B; $X_1, X_2, X_3, X_4 \ldots X_{38}$ represent the predictor variables shown in the questionnaire of Appendix A and Table 2 of Appendix B; and C represents the regression constant shown in Table 2 of Appendix B.

Next, the member is predicted to be high-risk or low-risk according to whether his or her resulting probability value $P_{high\_use}$ exceeds a threshold value that is determined a priori. The threshold value was selected to strike the optimal balance between the sensitivity and specificity of the measure. The probability values for the entire weighted respondent population ranged from 0.06 to 0.99 with a mean of 0.53, median of 0.52 and a standard deviation of 0.18. Various threshold values were evaluated for their efficacy using these parameters resulting in a selection of 0.47 as the final probability threshold value. This resulted in 59.9% of the entire weighted respondent population classified as high-risk, which when extrapolated to the entire population equaled approximately 6.9% of the total member population. This confirms, as stated previously, that the study sample had a disproportionate number of past and subsequent high care utilizers.

To test the predictive validity of the predictive model and the HMS 100, the formula was tested on both halves of the population with the Chi Square test using predicted (0,1) vs. observed (0,1) care use groups. In the first split-half (see Table 3 of Appendix B), the formula resulted in 72.5% (sensitivity) of the high-risk group predicted correctly and 52.7% (specificity) of the low-risk group. Positive predictive value was 63.5% and negative predictive value was 62.9%. In the second split-half, the formula resulted in 64.2% (sensitivity) of the high-risk group predicted correctly and 46.7% (specificity) of the low-risk group. Positive predictive value was 57.3% and negative predictive value was 53.9%.

For the total weighted population, the predicted high-risk members have significantly higher encounters and dollars than the low-risk group as detailed in Table 4. High-risk group average encounters exceeded the low-risk group by nearly 3 encounters as well as an average of $301 more in average care use dollars. Reduction in these dollars by even a net 25% through proactive intervention would have netted this health plan conservatively a half million dollars annually.

Moreover, the selection of 0.47 for the probability threshold value resulted in approximately 7% of the study population potentially needing prospective health advocacy. Accordingly, the health perception questionnaire and the HMS 100 are effective in identifying individuals at high risk for future high near-term care use without placing an exorbitant burden upon proactive case managers.

To test the health perception model of the exemplary HMS 100 against more traditional stratification methods, a logistic model was developed which used merely traditional predictor variables. The predictor variables used were previous hospitalization in the last six months, age, and presence of a chronic disease. At a probability threshold value of 0.56, sensitivity was 60.1% and specificity was 51.1%. Results showed that compared to the traditional method of identifying high-risk members, the health perception model of the exemplary HMS 100 added 12.4% to the sensitivity and 1.6% to the specificity in the first split-half, thus contributing considerable predictive power. In addition, because the exemplary HMS 100 uses self-reported information versus claims data, the time lag from assessment to intervention is shortened from several months to less than 24 hours from the initiation of data collection. Care providers also are not subsequently required to complete an additional health assessment, because the exemplary HMS 100 provides prescriptive as well as predictive information to guide health-counseling efforts.

While the invention has been illustrated and described in detail in the drawings and foregoing description, such illustration and description is to be considered as exemplary and not restrictive in character, it being understood that only exemplary embodiments have been shown and described and that all changes and modifications that come within the spirit of the invention are desired to be protected.

APPENDIX A

HEALTH PERCEPTION QUESTIONNAIRE

Part One: Tell us how you're feeling and doing

Please complete each section.
We want to ask you:
    How you are feeling and doing-compared with how you expect to be feeling and doing.
    Health is experienced as some level of illness or wellness. For example, a person can feel
    "well", that is be feeling good and doing what they are usually able to do, even
    though he or she may have a disease like diabetes or heart disease. At other time,
    a person who does not have a disease can feel "ill".

Tell us how you're doing

1) Think about your normal ability to do things. How have you been able
to do things IN THE PAST MONTH? (Your "normal" ability is what you are usually
able to do.)    Response box: 1,2,3,4, and 5
    1 = A lot less than my normal ability
    2 = A little less than my normal ability
    3 = At my normal ability
    4 = A little above my normal ability
    5 = Quite a bit better than my normal ability $X_{38}$    a) Physical ability (for example, walk, walk up stairs, vacuum, care for self, lift objects, mow lawn)
    b) Mental ability (for example, think, learn new things, solve problems, make decisions)
    c) Social ability (for example, get along with others, enjoy social activities, talk with others, meet your role responsibilities)
    d) Spiritual ability (for example, have a sense of meaning or purpose in life, have a sense of inner peace)

$X_7$    e) Personal needs ability (for example, spend time with family, sleep/rest, and leisure/free time activities)

2) To what extent has "feeling stressed" affected your ability to function overall
in the areas listed above?
    0 = Have not felt stressed $X_8$    1 = Have felt stressed, but has not limited my ability
    2 = Have felt stressed, and has slightly limited my ability
    3 = Have felt stressed, and has moderately limited my ability
    4 = Have felt stressed, and has greatly limited my ability

Tell us how you're feeling

Your physical symptoms

1) This question is about whether you are feeling any of the physical symptoms
listed below. First, review the list below and if you have not felt any of the symptoms
DURING THE PAST MONTH, mark the response below and move on to
Question 1 on the next page.
    ○ I have not felt any of the symptoms listed below DURING THE PAST MONTH.
Next, for every symptom you have felt DURING THE PAST MONTH, please
mark: 1) How often you have had each symptom, and 2) How much discomfort you have had from each symptom.
It is only necessary to mark those symptoms you are feeling - LEAVE ALL
OTHER SYMPTOMS BLANK.

| | A multiplied by B | |
|---|---|---|
| Symptom | How often have you felt this discomfort?<br>1 = Rarely felt<br>2 = Sometimes felt<br>3 = Frequently felt<br>4 = Constantly felt | How much discomfort have you had?<br>1 = Slight discomfort<br>2 = Mild discomfort<br>3 = Moderate discomfort<br>4 = Extreme discomfort |
| a) Change in urination habits | _____ | _____ |
| b) Chest pain/chest discomfort | _____ | _____ |
| c) Dizziness/light headedness | _____ | _____ |
| d) Drowsiness | _____ | _____ |
| $X_{17}$ e) Frequent back pain | _____ | _____ |
| f) Frequent coughing/wheezing | _____ | _____ |
| g) Headache | _____ | _____ |
| $X_{15}$ h) Indigestion | _____ | _____ |
| i) Nausea/vomiting | _____ | _____ |
| j) Obvious change in a mole | _____ | _____ |
| k) Pain other than chest or back paid (including cramping, aching) | _____ | _____ |
| l) Passing blood in stool | _____ | _____ |
| m) Persistent constipation | _____ | _____ |

APPENDIX A-continued

HEALTH PERCEPTION QUESTIONNAIRE $X_{16}$    n) Persistent diarrhea _____ _____
        o) Shortness of breath/difficulty _____ _____
        breathing
        p) Skin sore that doesn't heal _____ _____
        q) Thickening or lump in breast _____ _____
$X_{14}$    r) Tired/fatigued/weakness _____ _____
        s) Trouble with vision (even while _____ _____
        wearing glasses or contacts)
        t) Unexplained weight loss of more _____ _____
        than 10 lbs.
        u) Unusual bleeding or discharge _____ _____

Your medical conditions and how you care for yourself

1) This question is about whether you currently have any of the medical conditions listed below. First, review the list below and if you do not have any of the medical conditions listed, mark the response below and move on to Question 2 on this page. (unmarked = 0, marked = 1)

$X_{19}$    ○ I do not have any of the medical conditions listed below.

It is only necessary to mark those medical conditions you currently have please mark ALL that apply-LEAVE ALL OTHERS BLANK.

○ a) Allergies
$X_{21}$    ○ b) Arthritis
        ○ c) Asthma
        ○ d) Cancer
        ○ e) Cataracts
        ○ f) Chronic back problems
$X_{23}$    ○ g) Chronic lung disease
        ○ h) Coronary heart disease, congestive heart failure, angina, heart attack, or heart surgery
        ○ i) Deafness
        ○ j) Depression
$X_{20}$    ○ k) Diabetes or high blood sugar
        ○ l) High blood cholesterol of 240 or higher
$X_{22}$    ○ m) High blood pressure of 140/90 or higher
        ○ n) Kidney disease
        ○ o) Osteoporosis
        ○ p) Psychiatric illness other than depression
        ○ q) Seizures or epilepsy
        ○ r)Stroke
        ○ s) Ulcer or bowel/stomach bleeding
$X_{24}$    ○ t) Other _____ (please print clearly)

2) ○ Overall, how adequately do you feel you are managing your medical condition(s)? (Managing your medical condition(s) adequately means that you understand your condition and participate in your care.) Choose only one.
     0 = I do not currently have a medical condition(s), so this question does not apply to me.
     1 = More than adequately
     2 = Adequately
     3 = Somewhat adequately
     4 = Not at all adequately $X_{25}$    3) When given long-term medication, which statement is most like you? Choose only one.
     0 = I have never been given long-term medication, so this question does not apply to me.
     1 = I give myself reminders so I remember to take the medicine
     2 = I usually remember on my own
     3 = I don't pay much attention unless I get worse
     4 = I often forget to take my medicine
     5 = I sometimes stop taking my medicine on my own
     6 = I usually don't take the medicine at all.

4) How adequately do you feel you are currently managing your long-term medication(s)? (Managing your medication(s) adequately means that you understand how to take your medicine and you report how you're doing to your doctor.) Choose only one.
     0 = I am not currently on any long-term medication(s), so this question does not apply to me
     1 = More than adequately
     2 = Adequately
     3 = Somewhat adequately
     4 = Not at all adequately Your emotions 1) DURING THE PAST MONTH, how much have you felt each of the following?
     0 = Not felt
     1 = slightly
     2 = Somewhat
     3 = Quite a bit
     4 = Greatly

APPENDIX A-continued

HEALTH PERCEPTION QUESTIONNAIRE $X_{12}$     a) Afraid
        b) Angry
        c) Calm
$X_{11}$     d) Depressed
        e) Frustrated
$X_{13}$     f) Guilty
$X_{10}$     g) Happy
$X_9$     h) Sad

Part Two: Tell us about your health care visits and preferences

Please complete each section.

Your health care visits $X_2$     1) How many visits to a family doctor or specialist have you made IN THE PAST 6 MONTHS? (0-99)

$X_3$     1a) Think about those visits-how many did you initiate because of concerns you had or because you didn't feel well? (0-99)

2) How many visits have you made to the emergency room IN THE PAST 6 MONTHS? (0-99)

$X_1$     3) How many days have you been in the hospital due to sickness or injury IN THE PAST 6 MONTHS? (0-999)

$X_6$     4) How many days have you missed work or stayed home because you didn't feel well IN THE PAST 6 MONTHS? (0-999)

Your health care beliefs and preferences $X_{26}$     1) Which statement best describes your faith in doctors in general when you are dealing with a medical problem that you aren't sure about? Choose only one.
        1 = I don't believe what doctors tell me at all.
        2 = I believe what doctors tell me is often wrong.
        3 = I'm not sure if doctors are more often right or wrong.
        4 = I believe what doctors tell me is usually right.
        5 = I believe all of what doctors tell me.

$X_{27}$     2) Which statement best describes your opinion of the effectiveness and safety of medicine in general? Choose only one.
        1 = Most medical treatments have not been proven and might be harmful.
        2 = Many medical treatments may have harmful effects we don't know about.
        3 = Some medical treatments haven't been proven, but most are safe.
        4 = Most medical treatments have been proven to be effective and safe.

3) When facing an important medical issue, how often do you seek information from the following sources?
        0 = Never
        1 = Occasionally
        2 = Sometimes
        3 = Always
        a) Alternative Provider (for example, chiropractor, nutritionist, acupuncturist, etc.)
        b) Computer or Internet-based services
        c) Co-workers
        d) Doctor
        e) Family
        f) Friends
        g) Nurse
$X_{28}$     h) Printed materials
$X_{29}$     i) Telephone information services
$X_{30}$     j) Videos 4) Please rate your feelings about the following statements:
        1 = Strongly agree
        2 = Agree
        3 = Disagree
        4 = Strongly disagree
$X_{31}$     a) As you become sicker, you should be told more about your illness.
$X_{32}$     b) Even if the news is bad, you should be well informed
$X_{33}$     c) When you are caring for a family member, it is important to understand everything about their illness and treatment.

$X_{35}$     5) When you talk to your doctor about a health problem, how much information do you usually receive? Choose only one.
        1 = Less than I would like
        2 = The right amount
        3 = More than I would like $X_{36}$     6) For a minor illness, who should be making decisions about your care? Choose only one.
        1 = The doctor alone
        2 = Mostly your doctor
        3 = You and your doctor equally
        4 = Mostly you
        5 = You alone

APPENDIX A-continued

HEALTH PERCEPTION QUESTIONNAIRE $X_{37}$    7) When making a significant decision about health, which statement best describes you. Choose only one.
1 = I have not yet had to make an important medical care decision.
2 = I take as much time as I need to get as many opinions as I can and consider all my options carefully before I move ahead.
3 = I get a few opinions from key people, choose an action and then move ahead.
4 = I take action as quickly as possible based upon all the information I have at the time $X_{34}$    8) How much information would you like to receive about a serious medical problem? Choose only one.
1 = None
2 = Very little
3 = A fair amount
4 = Quite a lot
5 = All there is to know

Part Three: Tell us about your health practices and interests.

1) For each statement below, please tell us whether you already do or intend to do the following health practices. For each statement, please also tell us if you are interested in more information on that topic.
1 = Yes, I have for 5 or more years.
2 = Yes, I have for more than 6 months, but less than 5 years
3 = Yes, I have, but for less than 6 months
4 = No, but I intend to improve in the next 30 days
5 = No, but I intend to improve in the next 6 months
6 = No, and I do not intend to improve in the next 6 months
Check box: I am interested in more information on this topic
With respect to your overall lifestyle, do you . . .

a) Wear seat belts whenever you are in a motor vehicle?
$X_{18}$    b) Have your blood pressure checked regularly?
c) Have your blood cholesterol checked regularly?
d) Get regular health exams appropriate for your gender and age? (Examples are: mammograms, pap smears, prostate, rectal exams)
e) Use self-care information to avoid unnecessary doctor visits?
f) Watch your body for the seven warning signs of cancer?
g) Avoid eating high-fat foods?
h) Avoid being overweight for your height and frame size?
i) Exercise moderately at least three times a week for 30 minutes?
j) Avoid smoking or tobacco use? (If you have never smoked, mark 1)
k) Get 7 to 8 hours of sleep most days?
l) Use measures to protect your back when lifting heavy objects?
m) Have a working smoke detector near your sleeping area?
n) Have not more than 15 drinks per week if a man or 12 drinks per week if a woman? (If you have never consumed alcohol, mark 1.)
o) Avoid driving after having to much to drink, or riding with such a person?
p) Avoid using drugs to relieve stress or to alter sleep or for recreational use? (If you have never used drugs for these reasons, mark 1.)
q) Have people in your life you can call upon to share problems with or to get help if needed?
r) Cope well with stress on a regular basis?
s) Deal well with emotions such as anxiety, fear, guilt, frustration or anger?
t) Generally find meaning in your life?

Part Four: Tell us about yourself

It is very important that you accurately complete this section.
1) Name (Last Name, First Name, MI.)
2) Personal ID/SS No.
3) Group ID number (if applicable)
4) Today's Date
5) Age (years)

$X_4$    6) Gender
$X_5$    0 = male
       1 = female
7) Race (Optional)
1 = White
2 = Black, African American, Negro
3 = Asian
4 = Hispanic
5 = American Indian or native American
6 = Pacific Islander
7 = Other, please print_____
8) Education in Years (Optional)
For example, high school = 12 years; trade school = 13 years; bachelor's degree =16 years
9) Income (Optional)
1 = Under $20,000
2 = $20,000-$39,999

APPENDIX A-continued

HEALTH PERCEPTION QUESTIONNAIRE

3 = $40,000-$59,999
4 = $60,000-$79,999
5 = $80,000 or more

APPENDIX B

TABLE 1

Sample Descriptives: Unweighted and Weighted for Gender

| Characteristics: | Unweighted N | Percent | Weighted N | Percent |
|---|---|---|---|---|
| Total Population: | 20,000 | 100.0% | | |
| Total Respondents: | 4,210 | 21.1% | 6,312 | |
| Gender | | | | |
| Male | 1,043 | 24.8% | 3,129 | 49.6% |
| Female | 3,159 | 75.0% | 3,159 | 50.0% |
| Missing | 8 | .2% | 24 | .4% |
| Age | | | | |
| Mean age | 45.3 | | 46.4 | |
| Median age | 46.1 | | 47.3 | |
| Std. Deviation | 10.4 | | 10.3 | |
| Age range | 18.8-65.2 | | 18.8-65.2 | |
| Missing | 8 | | 24 | |
| Ethnicity | | | | |
| White | 3,499 | 83.1% | 5,239 | 83.0% |
| Black, African American, or Negro | 273 | 6.5% | 401 | 6.4% |
| Asian | 22 | .5% | 38 | .6% |
| Hispanic | 146 | 3.5% | 228 | 3.6% |
| American Indian or Native American | 18 | .4% | 36 | .6% |
| Other | 38 | .9% | 56 | .9% |
| Missing | 214 | 5.1% | 314 | 5.0% |
| Education | | | | |
| Mean years of education | 14.4 | | 14.4 | |
| Median years of education | 14.0 | | 14.0 | |
| Std. Deviation | 2.7 | | 2.8 | |
| Education range | 0-30 | | 0-30 | |
| Percentiles | | | | |
| $25^{th}$ | 12.0 | | 12.0 | |
| $50^{th}$ | 14.0 | | 14.0 | |
| $75^{th}$ | 16.0 | | 16.0 | |
| Missing | 257 | | 383 | |
| Subsequent 6 month Total Encounters | | | | |
| Mean | 8.5 | | 8.4 | |
| Median | 6.0 | | 6.0 | |
| Std. Deviation | 8.7 | | 8.9 | |
| Range | 1-128 | | 1-128 | |
| Percentiles | | | | |
| $25^{th}$ | 3.0 | | 3.0 | |
| $50^{th}$ | 6.0 | | 6.0 | |
| $75^{th}$ | 11.0 | | 10.0 | |
| Subsequent 6 month Total Claims Dollars | | | | |
| Mean | $832 | | $858 | |
| Median | $237 | | $230 | |
| Std. Deviation | $2,329 | | $2,495 | |
| Range | $0-$56,821 | | $0-$56,821 | |
| Percentiles | | | | |
| $25^{th}$ | $102 | | $98 | |
| $50^{th}$ | $237 | | $230 | |
| $75^{th}$ | $630 | | $631 | |

TABLE 2

Logistic Model of Predictors of the Probability
Of Becoming a High Encounter User within Six Months

| Predictors: | Original Range | Predictor Variable Assignment |  |  | Regression Coefficient | Coefficient Value |
|---|---|---|---|---|---|---|
| | | Variable | Assign 1 | Assign 0 | | |
| Past care use predictors: | | | | | | |
| Hospitalized in the past 6 months | 0-999 | $X_1$ | 2-999 | 0-1 | $\beta_1$ | .4665 |
| Visits to physician in the past 6 months | 0-99 | $X_2$ | 6-99 | 0-5 | $\beta_2$ | .8483 |
| Visits to physician initiated by member because of concerns | 0-99 | $X_3$ | 5-99 | 0-4 | $\beta_3$ | -.2624 |
| Demographic predictors: | | | | | | |
| Age | 0-199 | $X_4$ | | 0-199 | | |
| 60.0001 or more years | | | | | $\beta_4$ | 0 |
| 50.0001-60 years | | | | | $\beta_4$ | -.2986 |
| 40.0001-50 years | | | | | $\beta_4$ | -.4798 |
| 30.0001-40 years | | | | | $\beta_4$ | -.7207 |
| 30 or less years | | | | | $\beta_4$ | -.6724 |
| Gender | 0-1 | $X_5$ | 1 | 0 | $\beta_5$ | .4115 |
| Absence from work in past 6 months | 0-999 | $X_6$ | 2-999 | 0-1 | $\beta_6$ | .2326 |
| Perceived Health predictors: | | | | | | |
| Level of personal functioning | 1-5 | $X_7$ | 1 | 2-5 | $\beta_7$ | -.3915 |
| Feeling stressed | 0-4 | $X_8$ | 0-2 | 3-4 | $\beta_8$ | .4262 |
| Feeling Sad | 0-4 | $X_9$ | 2-4 | 0-1 | $\beta_9$ | -.2154 |
| Feeling Happy | 0-4 | $X_{10}$ | 0-1 | 2-4 | $\beta_{10}$ | .2038 |
| Feeling Depressed | 0-4 | $X_{11}$ | 2-4 | 0-1 | $\beta_{11}$ | -.3643 |
| Feeling Afraid | 0-4 | $X_{12}$ | 2-4 | 0-1 | $\beta_{12}$ | .2681 |
| Feeling Guilty | 0-4 | $X_{13}$ | 2-4 | 0-1 | $\beta_{13}$ | -.3581 |
| Tiredness | 0-16 | $X_{14}$ | 0-8 | 9-16 | $\beta_{14}$ | .6502 |
| Indigestion | 0-16 | $X_{15}$ | 0-8 | 9-16 | $\beta_{15}$ | .4265 |
| Diarrhea | 0-16 | $X_{16}$ | 0-8 | 9-16 | $\beta_{16}$ | .5226 |
| Drowsiness | 0-16 | $X_{17}$ | 0-8 | 9-16 | $\beta_{17}$ | -.7959 |
| Disease/compliance predictors: | | | | | | |
| Regular blood pressure checks | 1-6 | $X_{18}$ | 4-6 | 1-3 | $\beta_{18}$ | -.4244 |
| No disease conditions | 0-1 | $X_{19}$ | 0 | 1 | $\beta_{19}$ | -.4186 |
| Diabetes | 0-1 | $X_{20}$ | 1 | 0 | $\beta_{20}$ | .8025 |
| Arthritis | 0-1 | $X_{21}$ | 1 | 0 | $\beta_{21}$ | -.1828 |
| Hypertension | 0-1 | $X_{22}$ | 1 | 0 | $\beta_{22}$ | -.2132 |
| Chronic lung disease | 0-1 | $X_{23}$ | 1 | 0 | $\beta_{23}$ | .4641 |
| Other diseases | 0-1 | $X_{24}$ | 1 | 0 | $\beta_{24}$ | .2071 |
| Medication compliance | 0-6 | $X_{25}$ | 0-2 | 3-6 | $\beta_{25}$ | -.5362 |
| Belief/Preference predictors: | | | | | | |
| Faith in the care system | 1-5 | $X_{26}$ | 1-3 | 4-5 | $\beta_{26}$ | .3306 |
| Effectiveness and safety of care | 1-4 | $X_{27}$ | 1-2 | 3-4 | $\beta_{27}$ | .2235 |
| Seek information from printed material | 0-3 | $X_{28}$ | 0-1 | 2-3 | $\beta_{28}$ | .1441 |
| Seek information from phone information services | 0-3 | $X_{29}$ | 0-1 | 2-3 | $\beta_{29}$ | -.3793 |
| Seek information from videos | 0-3 | $X_{30}$ | 0-1 | 2-3 | $\beta_{30}$ | -.6228 |
| Told more as you become sicker | 1-4 | $X_{31}$ | 3-4 | 1-2 | $\beta_{31}$ | .3322 |
| Well informed even if bad news | 1-4 | $X_{32}$ | 3-4 | 1-2 | $\beta_{32}$ | 1.9274 |
| Should have treatment information when caring for family member | 1-4 | $X_{33}$ | 3-4 | 1-2 | $\beta_{33}$ | -1.0287 |
| Preference for amount of information for serious medical problem | 1-5 | $X_{34}$ | 1-3 | 4-5 | $\beta_{34}$ | 1.8249 |
| Preference for amount of information received from doctor | 1-3 | $X_{35}$ | 1,3 | 2 | $\beta_{35}$ | -.1790 |
| Who should make care decisions with minor illness | 1-5 | $X_{36}$ | 1,5 | 2-4 | $\beta_{36}$ | -.4005 |
| Time to make significant health decision | 1-4 | $X_{37}$ | 2-4 | 1 | $\beta_{37}$ | -.2932 |
| Interaction predictors: | | | | | | |
| Age by level of physical functioning | 1-5 | $X_{38}$ | 1 | 2-5 | | |
| 60.0001 or more years | | | | | $\beta_{38}$ | 0 |
| 50.0001-60 years | | | | | $\beta_{38}$ | .7472 |
| 40.0001-50 years | | | | | $\beta_{38}$ | .4277 |
| 30.0001-40 years | | | | | $\beta_{38}$ | 1.3903 |
| 30 or less years | | | | | $\beta_{38}$ | .0424 |
| Hospitalization by visits to physician | | | | | $\beta_{39}$ | -1.5563 |
| Constant | | | | | C | 1.1724 |

TABLE 3

Results of Chi Square for Predicted vs. Observed Care Use Groups for Split-Half-1

| Observed care use groups | | Predicted care use groups | | |
|---|---|---|---|---|
| | | Low (0) | High (1) | Total |
| Low (0) | Count | 769 | 689 | 1458 |
| | % Within observed group | 52.7% | 47.3% | 100.0% |
| | % Within predicted group | 62.9% | 36.5% | 46.9% |
| | % Of Total | 24.7% | 22.2% | 46.9% |
| High (1) | Count | 454 | 1197 | 1651 |
| | % Within observed group | 27.5% | 72.5% | 100.0% |
| | % Within predicted group | 37.1% | 63.5% | 53.1% |
| | % Of Total | 14.6% | 38.5% | 53.1% |
| Total | Count | 1223 | 1886 | 3109 |
| | % Within observed group | 39.3% | 60.7% | 100.0% |
| | % Within predicted group | 100.0% | 100.0% | 100.0% |
| | % Of Total | 39.3% | 60.7% | 100.0% |

TABLE 4

ANOVA: Differences in Care Use between Predicted High vs. Low Risk Groups

| | | Sum of Squares | df | Mean Square | F | Sig. |
|---|---|---|---|---|---|---|
| Encounters | Between groups | 10047.02 | 1 | 10047.02 | 130.024 | .000 |
| | Within groups | 487578.09 | 6310 | 77.271 | | |
| | Total | 497625.11 | 6311 | | | |
| Dollars | Between groups | 1.38E+08 | 1 | 137655738.62 | 22.179 | .000 |
| | Within groups | 3.92E+10 | 6310 | 6206462.045 | | |
| | Total | 3.93E+10 | 6311 | | | |

| | High-Risk Group (Weighted) (N = 3,778) | Low-Risk Group (Weighted) (N = 2,534) |
|---|---|---|
| Encounters over six months (mean) | 9.41 | 6.83 |
| Dollars over six months (mean) | $979.29 | $678.03 |

What is claimed is:

1. A method of improving health and reducing healthcare encounter trends, comprising the steps of:

presenting an individual with a questionnaire designed to elicit said individual's response to each distinct predictive factor of a predetermined set of predictive factors, said predetermined set of predictive factors including domains of functional ability, adherence with current medical treatment, numbers of uses of various healthcare services over past time periods, beliefs in the safety and value of healthcare services, healthcare partnering preferences and information-seeking preferences;

collecting self-reported information from said individual about their perceived health wherein said self-reported information comprises said individual's response to each said distinct predictive factor of said predetermined set of predictive factors;

assigning, based upon said individual's response, a dichotomous value to each said distinct predictive factor of said predetermined set of predictive factors;

calculating, based upon a predetermined predictive model and said dichotomous values assigned to said predetermined set of predictive factors, a probability value of said individual becoming a high-encounter user of healthcare services for any reason within a prospective time span, wherein a high-encounter user makes high use of inpatient, outpatient, emergency room, or physician office healthcare services, and wherein said calculating is accomplished using a computing device having a processor;

and identifying said individual as a probable high-encounter user of healthcare services within said prospective time span if said probability value of said individual exceeds a predetermined threshold.

2. The method of claim 1, wherein said collecting step comprises the step of:

presenting said individual with a self assessment questionnaire designed to elicit said information from said individual for said predetermined set of predictive factors.

3. The method of claim 1, wherein said collecting step comprises the step of:

presenting, to a web browser, a questionnaire that elicits said information from said individual for said predetermined set of predictive factors;

receiving, via said web browser, said information for said predetermined set of predictive factors in response to said presenting step.

4. The method of claim 1, further comprising the steps of:

determining, based upon said information from said individual, at least one intervention program for said individual in response to said probability value exceeding said predetermined threshold.

5. The method of claim 1, wherein said generating step comprises:

generating, using said dichotomous values assigned to said set of predictive factors and a logistic regression formula of said predictive model, said probability value of said individual becoming a high-encounter user of healthcare services for any reason within said prospective time span.

6. The method of claim 1, wherein said generating step comprises:

defining a first reference date in the future; and generating, using said dichotomous values assigned to each said distinct predictive factor of said predetermined set of predictive factors, a probability value of said individual becoming a high-encounter user of healthcare services at a predetermined level for any reason in the time period between a present date and said first reference date.

7. The method of claim 1, further comprising:
presenting said individual with a self-assessment questionnaire designed to elicit said individual's response to each said distinct predictive factor of said predetermined set of predictive factors, said self-assessment questionnaire including a plurality of questions;
collecting a plurality of answers to said self-assessment questionnaire from each of a plurality of sample subjects;
collecting a total number of healthcare encounters within a predetermined time span for each of said plurality of sample subjects, an encounter being a use of inpatient, outpatient, emergency room, or physician office healthcare services by said sample subject;
determining a dependent variable during derivation of said predetermined predictive model, said dependent variable being based on said total number of healthcare encounters within a predetermined time span for each of said plurality of sample subjects;
determining, based on said plurality of answers from each of said plurality of sample subjects, said predetermined set of predictive factors from a larger set of potential predictive factors during derivation of a logistic regression formula for said predictive model; and
deriving said logistic regression formula for said predictive model from said dependent variable and said predetermined set of predictive factors, said predictive model being designed to predict said probability value of a person becoming a high-encounter user of healthcare services for any reason within a prospective time span.

8. The method of claim 7, wherein said total number of healthcare encounters for each particular subject of said plurality of sample subjects is equal to a total of the times said particular subject used a unique healthcare service provider on a unique date within said predetermined time span.

9. A method of improving health and reducing healthcare encounter trends, the method comprising:
designing a self-assessment questionnaire comprising a plurality of questions designed to elicit self-reported information from an individual about their perceived health;
presenting each of a plurality of sample subjects with the self-assessment questionnaire;
collecting a plurality of answers from each of the plurality of sample subjects answering the plurality of questions of the self-assessment questionnaire;
collecting from healthcare claims data, a total number of healthcare encounters for each of the plurality of sample subjects during a predetermined time span, the total number of healthcare encounters being the sum of all uses of inpatient, outpatient, emergency room, and physician office healthcare services by the sample subject within the predetermined time span;
determining a dependent variable based on the total number of healthcare encounters for each of the plurality of sample subjects during the predetermined time span;
determining a set of independent predictor variables based upon the plurality of answers from the self-assessment questionnaire from each of the plurality of sample subjects;
associating each predictor variable of the set of independent predictor variables to at least one of the plurality of questions of the self-assessment questionnaire;
deriving a predictive modeling formula from the dependent variable and the set of independent predictor variables for each of the plurality of sample subjects, the predictive modeling formula being designed to determine a probability value for each individual of a plurality of individuals becoming a high-encounter user of healthcare services for any reason within a prospective time span, and wherein said deriving is accomplished using a computing device having a processor;
determining a threshold value such that the individual will be classified as a probable high-encounter user of healthcare services within the prospective time span if the probability value computed by the predictive modeling formula for the individual exceeds the threshold value;
programming a computing device having a processor with the predictive modeling formula and the threshold value for the purpose of using said computing device and said predictive modeling formula to identify individuals as probable high-encounter users of healthcare services within a prospective time span if said probability value of said individuals exceeds a predetermined threshold.

10. The method of claim 9, further comprising:
presenting a person with the self-assessment questionnaire to elicit self reported information from the person;
collecting a plurality of answers from the person answering the plurality of questions of the self-assessment questionnaire;
determining, based upon the plurality of answers, a dichotomous value for each predictor variable of the set of independent predictor variables;
assigning a first dichotomous value to each predictor variable for which the determining step determines that the self-reported information is indicative of the person being a high-encounter user of healthcare services within the prospective time span;
assigning a second dichotomous value to each predictor variable for which the determining step determines that the self reported information is not indicative of the person being a high-encounter user of healthcare services within the prospective time span;
generating, based upon the predictive modeling formula and the dichotomous values assigned to each of the predictor variables in the set of predictor variables, a probability value of the person being a high-encounter user of healthcare services within the prospective time span
comparing the probability value to the threshold value; and
identifying the person as a probable high-encounter user of healthcare services within the prospective time span if the probability value exceeds the threshold value.

11. The method of claim 10, further comprising:
assigning the first dichotomous value to each predictor variable for which the at least one of the plurality of questions associated with the predictor variable is unanswered or answered inappropriately.

12. The method of claim 10, further comprising:
identifying the person as a probable high-encounter-user of healthcare services if the person fails to answer more than a predetermined number of the plurality of questions of the self-assessment questionnaire.

13. The method of claim 10, wherein the collecting a plurality of answers step comprises:
presenting the self-assessment questionnaire to the person through a web browser; and
receiving the plurality of answers from the person in response to the presenting step through the web browser.

14. The method of claim 10, wherein the collecting a plurality of answers step comprises:
- presenting the self-assessment questionnaire to the person, the self-assessment questionnaire including a scannable form; and
- scanning the scannable form received in response to the presenting step to retrieve the plurality of answers from the person.

15. The method of claim 10, wherein the collecting a plurality of answers step comprises:
- presenting the self-assessment questionnaire to the person using an interactive voice response telephone system; and
- receiving the plurality of answers from the person using the interactive voice response telephone system.

16. The method of claim 10, wherein the plurality of questions of the self-assessment questionnaire includes questions directed to the domains of functional ability, adherence with past medical advice, number of encounters with various healthcare services over a certain period, beliefs in the safety and value of healthcare services and healthcare partnering and information seeking preferences.

17. The method of claim 16, wherein the questions directed to functional ability include questions directed to physical ability, mental ability, social ability, spiritual ability and personal needs ability in which the person is asked to rate their degree of functioning related to their normal ability in each such domain of functional ability.

18. The method of claim 10, wherein the predictive modeling function is derived using logistic regression.

19. The method of claim 18, wherein the predictive modeling function includes a formula represented by:

$$z = \beta_1 X_1 + \beta_2 X_2 + \beta_3 X_3 + \beta_4 X_4 \ldots \beta_N X_N + \beta_{N+1} X_1 X_2 + C,$$

$$P_{high\_use} = e^z/(1+e^z)$$

wherein $\beta_1, \beta_2, \beta_3, \beta_4 \ldots \beta_{N+1}$ represent regression coefficients, $X_1, X_2, X_3, X_4 \ldots X_N$ represent the set of predictor variables, and $P_{high\_use}$ represents the probability value of the person becoming a high-encounter user of healthcare services for any reason within the prospective time span.

* * * * *